United States Patent
Salamone et al.

(10) Patent No.: US 8,293,492 B2
(45) Date of Patent: Oct. 23, 2012

(54) LENALIDOMIDE AND THALIDOMIDE IMMUNOASSAYS

(75) Inventors: Salvatore J Salamone, Stockton, NJ (US); Jodi Blake Courtney, Doylestown, PA (US); Alexander Volkov, Allentown, PA (US); Howard Sard, Arlington, MA (US); Vishnumurthy Hegde, Chelmsford, MA (US)

(73) Assignee: Saladax Biomedical Inc., Bethlehem, PA (US)

( * ) Notice: Subject to any disclaimer, the term of this patent is extended or adjusted under 35 U.S.C. 154(b) by 0 days.

(21) Appl. No.: 13/302,844

(22) Filed: Nov. 22, 2011

(65) Prior Publication Data
US 2012/0064549 A1 Mar. 15, 2012

Related U.S. Application Data

(62) Division of application No. 12/722,829, filed on Mar. 12, 2010, now Pat. No. 8,114,621.

(51) Int. Cl.
*G01N 33/53* (2006.01)
*G01N 33/543* (2006.01)
*C07K 1/10* (2006.01)

(52) U.S. Cl. ........ 435/7.93; 435/7.1; 435/7.92; 436/501; 436/518; 436/523; 436/815; 530/388.9; 530/402; 530/403

(58) Field of Classification Search .................. None
See application file for complete search history.

(56) References Cited

U.S. PATENT DOCUMENTS
2006/0223134 A1* 10/2006 Salamone et al. ........... 435/7.92

OTHER PUBLICATIONS

Goodrow et al., "Strategies for Immunoassay Hapten Design," in Immunoanalysis of Agrochemicals; Nelson, J., et al.; ACS Symposium Series, 1995, vol. 586, Chapter 9, pp. 119-139.*
Lu et al., "Thalidomide Metabolites in Mice and Patients with Multiple Myeloma," Clin. Cancer Res., 2003, vol. 9, pp. 1680-1688.*

* cited by examiner

*Primary Examiner* — Mark Shibuya
*Assistant Examiner* — Galina Yakovleva

(57) ABSTRACT

Novel conjugates and immunogens derived from lenalidomide and antibodies generated by these immunogens are useful in immunoassays for the quantification and monitoring of thalidomide and lenalidomide in biological fluids.

19 Claims, No Drawings

LENALIDOMIDE AND THALIDOMIDE IMMUNOASSAYS

CROSS-REFERENCE TO RELATED APPLICATIONS

This Application is a divisional application of application Ser. No. 12/722,829, filed Mar. 12, 2010, now U.S. Pat. No. 8,114,621, issued Feb. 14, 2012, which is hereby incorporated by reference in its entirety. The priority of application Ser. No. 12/722,829 is claimed.

FIELD OF THE INVENTION

This invention relates to the field of immunoassays for determining the presence and/or quantifying the amount of lenalidomide and thalidomide in human biological fluids in order to rapidly determine optimal drug concentrations during treatment.

BACKGROUND OF THE INVENTION

Cancer is a term used to describe a group of malignancies that all share the common trait of developing when cells in a part of the body begin to grow out of control. Most cancers form as tumors, but can also manifest in the blood and circulate through other tissues where they grow. Cancer malignancies are most commonly treated with a combination of surgery, chemotherapy, and/or radiation therapy. The type of treatment used to treat a specific cancer depends upon several factors including the type of cancer malignancy and the stage during which it was diagnosed.

The chemotherapeutic agent whose common chemical name is thalidomide has the following formula:

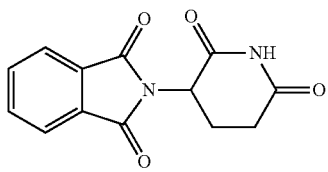

I

The chemotherapeutic agent whose common chemical name is lenalidomide has the following formula:

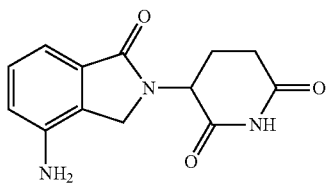

II

Thalidomide possesses immunomodulatory, anti-inflammatory and anti-angiogenic properties. The immunomodulatory and anti-inflammatory properties may be related to suppression of excessive tumor necrosis factor-alpha production through degradation of mRNA encoding the factor (Moreira, J Exp Med, 177(6): 1675-80, 1993). Other immunomodulatory and anti-inflammatory properties of thalidomide may include suppression of macrophage involvement in prostaglandin synthesis, and modulation of interleukin-10 and interleukin-12 production by peripheral blood mononuclear cells. The combination of anti-inflammatory and anti-angiogenic properties makes thalidomide a novel therapeutic agent with significant potential in treating a wide variety of diseases (Teo, Clin Pharmacokinet, 43(5): 311-27, 2004). A number of recent clinical trials have demonstrated therapeutic effect of thalidomide in patients with multiple myeloma, renal carcinoma and glioblastoma multiforme (Singhal, N Engl J Med, 341(21): 1565-71, 1999; Marx, J Neurooncol, 54(1): 31-8, 2001). Currently, thalidomide is approved for treatment of patients with newly diagnosed multiple myeloma and for acute treatment of erythema nodosum leprosum (Package-insert-Thalidomide, Celgene Corp., 2009).

Lenalidomide is a thalidomide derivative with immunomodulatory, anti-proliferative, and anti-angiogenic properties. Lenalidomide exerts direct anti-proliferative effect on multiple myeloma cells by inducing cell cycle arrest and apoptosis (Armoiry, J Clin Pharm Ther, 33(3): 219-26, 2008). Lenalidomide is approved for treatment of patients with multiple myeloma and myelodysplastic syndromes associated with a deletion 5q cytogenetic abnormality (Package-insert-Revlimid, Celgene Corp., 2009).

The mechanisms of action and metabolic pathways of thalidomide and lenalidomide are not fully characterized yet. In vivo, both drugs can undergo non-enzymatic hydrolysis and enzymatic metabolism producing a multitude of metabolites, but none of those compounds were found to be responsible for thalidomide therapeutic effect Lepper, Curr Drug Metab, 7(6): 677-85, 2006).

Thalidomide and lenalidomide exhibit significant variability in plasma concentrations. A phase I study of pharmacokinetic effects of thalidomide in HIV patients has demonstrated a wide range of maximum drug concentration $C_{max}$ (2.8±2.6 mg/L) and half-life time $t_{1/2}$ (5.9±2.3 hours) (Wohl, J Infect Dis, 185(9): 1359-63, 2002). Administration of thalidomide to healthy subjects resulted in up to 52% variability in $C_{max}$ and up to 37% variability in to (Package-insert-Thalidomide, Celgene Corp., 2009). A Phase I trial of lenalidomide in patients with central nervous system tumors has revealed up to 78% variability in $C_{max}$ and up to 122% variability in $t_{1/2}$ (Fine, Clin Cancer Res, 13(23): 7101-6, 2007).

Since efficacy of thalidomide and lenalidomide is improved at higher concentration levels and the drugs exhibit wide intra- and inter-patient pharmacokinetic variability monitoring concentrations of these drugs in blood and adjusting to target levels would be of value in increasing efficacy and minimizing toxicity. The degree of intra- and inter-individual pharmacokinetic variability of thalidomide and lenalidomide is impacted by many factors, including:

Age
Weight
Organ function
Drug-drug interaction
Genetic regulation
Compliance

As a result of this variability, equal doses of the same drug in different individuals can result in dramatically different clinical outcomes. The effectiveness of the same dosage of thalidomide and lenalidomide varies significantly based upon individual drug clearance and the ultimate serum drug concentration in the patient. Therapeutic drug management would provide the clinician with insight on patient variation in drug administration. With therapeutic drug management, drug dosages could be individualized to the patient, and the chances of effectively treating the disorder without the unwanted side effects would be much higher.

Routine therapeutic drug management of thalidomide and lenalidomide would require the availability of simple automated tests adaptable to general laboratory equipment. The use of liquid chromatography (LC) with UV or mass spectroscopy detection to determine the concentration of thalidomide and lenalidomide in human blood and plasma has been described (Tohnya, J Chromatogr B Analyt Technol Biomed Life Sci, 811(2): 135-41, 2004; Chen, J Clin Pharmacol, 47(12): 1466-75, 2007; Teo, J Clin Pharmacol, 39(11): 1162-8, 1999). These methods are labor intensive, requiring liquid-liquid or solid phase extractions, use expensive equipment and are not amenable to routine clinical laboratory use. To date, there are no immunoassays for measuring lenalidomide and/or thalidomide in human biological fluids of patients treated with these chemotherapeutic agents.

As seen from the foregoing, there are no immunoassays for determining the presence and/or quantifying the amount of thalidomide and lenalidomide in human biological fluids. Routine therapeutic drug management of thalidomide and lenalidomide by immunoassays would provide simple automated tests adapted to standard laboratory equipment. However, in order to provide such immunoassays, antibodies specific to thalidomide and lenalidomide must be produced. The derivatives and immunogen used in this assay must impart through these corresponding antibodies produced specific reactivity to thalidomide and lenalidomide.

SUMMARY OF INVENTION

In accordance with this invention, a new class of antibodies have been produced which are substantially reactive to thalidomide and lenalidomide and can be used in the same immunoassay to determine the presence and/or quantify the amount of thalidomide and lenalidomide in patients' samples treated with these chemotherapeutic drugs.

It has been found that by using immunogens which are conjugates of an immunogenic carrier containing polyamine polymer with a compound of the formula:

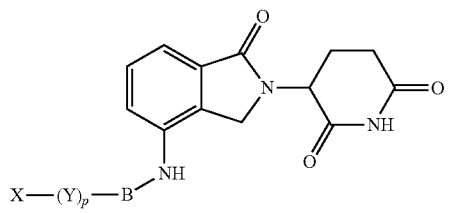

III wherein B is —C(=O)—CH2-, —C(=O)—NH—CH2-, —C(=O)—O—CH2- or —CH2-
Y is an organic spacing group;
p is an integer from 0 to 1;
X is a terminal functional group capable of binding to said polyamine polymer,
antibodies are produced which are specific for lenalidomide as well as mixtures of lenalidomide with thalidomide and are non reactive or non binding with pharmaceutically inactive metabolites of both thalidomide and lenalidomide.

The provision of these antibodies which are electively reactive with either lenalidomide or a mixture of thalidomide and lenalidomide, allows one to produce an immunoassay which can specifically detect and quantify so as to monitor thalidomide and lenalidomide in the fluid samples of patients being treated with either thalidomide or lenalidomide. Also included within this invention are reagents and kits for said immunoassay.

DETAILED DESCRIPTION

In accordance with this invention, a new class of antibodies is provided which selectively binds to lenalidomide or mixtures of lenalidomide with thalidomide and is not cross reactive with pharmaceutically inactive metabolites of either thalidomide and lenalidomide. It has been discovered that through the use of these derivatives of lenalidomide of formula III as immunogens, this new class of antibodies of this invention is provided. It is through the use of these antibodies that an immunoassay, including reagents and kits for such immunoassay for detecting and/or quantifying thalidomide and lenalidomide in blood, plasma or other body fluid samples has been developed.

In accordance with this invention a new class of reagents is provided which can be used in either of these immunoassays for detecting and/or quantifying thalidomide or lenalidomide in samples. This reagent is a conjugate of a carrier with a ligand having the formula:

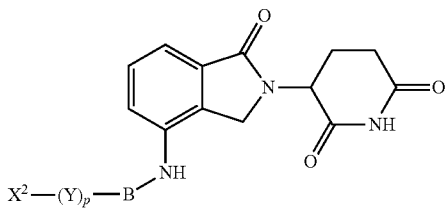

III-A wherein B, Y and P are as above and $X^2$ is a terminal functional group capable of binding to said carrier.

By use of this immunoassay, the presence and amount of thalidomide or lenalidomide in body fluid samples of patients being treated with either therapeutic agent can be detected and/or quantified. In this manner, a patient being treated with thalidomide or lenalidomide can be monitored during therapy and the treatment adjusted in accordance with said monitoring by using antibodies produced by the immunogen of formula III and the conjugate of Formula III-A. By means of this invention one achieves the therapeutic drug management of thalidomide and lenalidomide in patients being treated with either thalidomide or lenalidomide as therapeutic agents. The therapeutic agents to be detected and/or quantified are thalidomide of formula I and lenalidomide of formula II.

The provision of the conjugates of formulae III-A as a reagent in the immunoassay and the immunogen of Formula III conjugated with an immunogenic carrier provides antibodies and reagents which can be utilized in immunoassays to detect and/or quantify the chemotherapeutic agents lenalidomide and thalidomide. These reagents and the antibodies produced in accordance with this invention can be utilized both in immunoassays for detecting and quantifying lenalidomide or thalidomide. In general, patients are treated with one and not both of these chemotherapeutic agents. Therefore, an antibody or reagent which is selectively reactive against both lenalidomide and thalidomide can be utilized in these immunoassays to detect either lenalidomide or thalidomide. This is true, since a patient treated lenalidomide is not generally treated with thalidomide and a patient treated with thalidomide is not generally treated lenalidomide. Therefore, the reagents and antibodies of this invention can be used in either of these two immunoassays to separately detect and/or quantify these two chemotherapeutic agents.

As set forth hereinbefore, the antibodies that can be produced by the immunogen of formula III are selectively reactive with lenalidomide and mixtures of thalidomide with lenalidomide and can be used in either an immunoassay for thalidomide or for lenalidomide. While these antibodies are selectively reactive with both thalidomide and lenalidomide, in order to be used in an immunoassay for thalidomide, the antibody should have a selective reactivity of at least about 10%, preferably at least about 40%, for thalidomide, based upon its combined reactivity with both thalidomide and lenalidomide. In accordance with this invention, antibodies can be produced utilizing the immunogen of formula III having reactivity with thalidomide of at least about 10%, and at most about 50%, based upon their reactivity with both lenalidomide and thalidomide.

On the other hand for utilizing an antibody in an immunoassay for lenalidomide, any of the antibodies produced by the immunogen of formula III having a selective reactivity with lenalidomide or with both lenalidomide and thalidomide can be used. In accordance with this invention antibodies which are selectively reactive with lenalidomide based upon their reactivity with thalidomide and lenalidomide or selectivity reactive with both lenalidomide and thalidomide can be produced by means of the immunogen of formula III. In accordance with this invention an antibody which is selectively reactive with lenalidomide and not thalidomide, i.e., antibodies having 100% selective reactivity with lenalidomide based upon their selective reactivity with both lenalidomide and thalidomide can be produced by use of the immunogen of formula III. The antibodies having substantially 100% selective reactivity with lenalidomide and substantially no selective reactivity with thalidomide are especially preferred for use in the immunoassay for lenalidomide.

The reagents utilized in the assays of this invention are conjugates of a polymeric carrier with the compounds of formula III-A. These conjugates are competitive binding partners with the thalidomide or lenalidomide present in the sample for the binding with the antibodies of this invention. Therefore, the amount of this conjugate reagent which binds to the antibody will be inversely proportional to the amount of thalidomide or lenalidomide in the sample. In accordance with this invention, the assay utilizes any conventional measuring means for detecting and measuring the amount of said conjugate which is bound or unbound to the antibody. Through the use of said means, the amount of the bound or unbound conjugate can be determined. Generally, the amount of thalidomide and lenalidomide in a sample is determined by correlating the measured amount of the bound or unbound conjugate produced by the thalidomide or lenalidomide in the sample with values of the bound or unbound conjugate determined from a standard or calibration curve obtained with samples containing known amounts of thalidomide or lenalidomide, which known amounts are in the range expected for the sample to be tested. These studies for producing calibration curves are determined using the same immunoassay procedure as used for the sample.

The conjugates, as well as the immunogens, are prepared from compounds of the formula III. When in the conjugates or immunogens, the carrier and the polyamine polymer are linked to ligand portions of the compounds of formula III, this ligand portions has the formula:

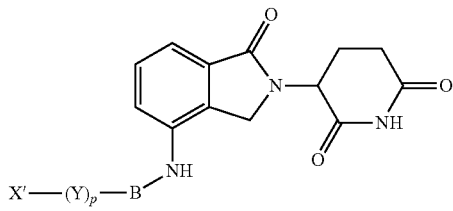

wherein X' is —CH$_2$— or a functional linking group; and Y, p and B, are as above This ligand portion may be linked to one or more active sites on the carrier of the conjugate or the immunogen. Generally these carriers contain polymers, most preferably polyamine polymers having a reactive amino group. In forming the conjugates especially the immunogen, X' is preferably a functional group which can react with an amino group. However with respect to the reagent used in the immunoassay, X' can be any functional group which can react with any conventional carrier. When the compound of formula III is used to make immunogens, X' in the compound of formula III is preferably any functional group capable of binding or linking to a polyamine polymer.

Definitions

Throughout this description the following definitions are to be understood:

The term "alkylene" designates a divalent saturated straight or branch chain hydrocarbon substituent containing from one to ten carbon atoms The terms "immunogen" and "immunogenic" refer to substances capable of eliciting, producing, or generating an immune response in an organism.

The term "conjugate" refers to any substance formed from the joining together of two parts. Representative conjugates in accordance with the present invention include those formed by the joining together of a small molecule, such as the compound of formula III or the compound of formula III-A and a large molecule, such as a carrier, preferably carriers which comprise a polyamine polymer, particularly a protein. In the conjugate the small molecule may be joined or linked at one or more active sites on the large molecule. The term conjugate includes the term immunogen. In the conjugates used as reagents the carrier can be any carrier and X can be any functional group which can be linked to a carrier. In the immunogen the carrier is a polyamine polymer and X is any functional group capable of linking to a polyamine polymer.

"Haptens" are partial or incomplete antigens. They are protein-free substances, mostly low molecular weight substances, which are not capable of stimulating antibody formation, but which do react with antibodies. The latter are formed by coupling a hapten to a high molecular weight immunogenic carrier and then injecting this coupled product, i.e., immunogen, into a human or animal subject. The hapten of this invention is lenalidomide (II).

As used herein, a "spacing group" or "spacer" refers to a portion of a chemical structure which connects two or more substructures such as haptens, carriers, immunogens, labels, or tracer through a CH$_2$ or functional linking group. These spacer groups will be enumerated hereinafter in this application. The atoms of a spacing group and the atoms of a chain within the spacing group are themselves connected by chemical bonds. Among the preferred spacers are straight or branched, saturated or unsaturated, carbon chains. Theses carbon chains may also include one or more heteroatoms within the chain or at termini of the chains. By "heteroatoms" is meant atoms other than carbon which are chosen from the group consisting of oxygen, nitrogen and sulfur. Spacing groups may also include cyclic or aromatic groups as part of the chain or as a substitution on one of the atoms in the chain.

The number of atoms in the spacing group is determined by counting the atoms other than hydrogen. The number of atoms in a chain within a spacing group is determined by counting the number of atoms other than hydrogen along the shortest route between the substructures being connected. A functional linking group may be used to activate, e.g., provide an available functional site on, a hapten or spacing group for synthesizing a conjugate of a hapten with a label or carrier or polyamine polymer.

An "immunogenic carrier," as the terms are used herein, is an immunogenic substance, commonly a protein, that can join with a hapten, in this case lenalidomide or the lenalidomide derivatives hereinbefore described, thereby enabling these hapten derivatives to induce an immune response and elicit the production of antibodies that can bind specifically with these haptens and to thalidomide. The immunogenic carriers and the linking groups will be enumerated hereinafter in this application. Among the immunogenic carrier substances are included proteins, glycoproteins, complex polyamino-polysaccharides, particles, and nucleic acids that are recognized as foreign and thereby elicit an immunologic response from the host. The polyamino-polysaccharides may be prepared from polysaccharides using any of the conventional means known for this preparation.

Also various protein types may be employed as a poly (amino acid) immunogenic carrier. These types include albumins, serum proteins, lipoproteins, etc. Illustrative proteins include bovine serum albumin (BSA), keyhole limpet hemocyanin (KLH), egg ovalbumin, bovine thyroglobulin (BTG) etc. Alternatively, synthetic poly(amino acids) may be utilized.

Immunogenic carriers can also include polyamino-polysaccharides, which are high molecular weight polymers built up by repeated condensations of monosaccharides. Examples of polysaccharides are starches, glycogen, cellulose, carbohydrate gums such as gum arabic, agar, and so forth. The polysaccharide also contains polyamino acid residues and/or lipid residues.

The immunogenic carrier can also be a poly (nucleic acid) either alone or conjugated to one of the above mentioned poly(amino acids) or polysaccharides.

The immunogenic carrier can also include solid particles. The particles are generally at least about 0.02 microns (μm) and not more than about 100 μm, and usually about 0.05 μm to 10 μm in diameter. The particle can be organic or inorganic, swellable or non-swellable, porous or non-porous, optimally of a density approximating water, generally from about 0.7 to 1.5 g/mL, and composed of material that can be transparent, partially transparent, or opaque. The particles can be biological materials such as cells and microorganisms, including non-limiting examples such as erythrocytes, leukocytes, lymphocytes, hybridomas, *Streptococcus, Staphylococcus aureus, E. coli*, and viruses.

The particles can also be comprised of organic and inorganic polymers, liposomes, latex, phospholipid vesicles, or lipoproteins.

"Poly(amino acid)" or "polypeptide" is a polyamide formed from amino acids. Poly(amino acids) will generally range from about 2,000 molecular weight, having no upper molecular weight limit, normally being less than 10,000,000 and usually not more than about 600,000 daltons. There will usually be different ranges, depending on whether an immunogenic carrier or an enzyme is involved.

A "peptide" is any compound formed by the linkage of two or more amino acids by amide (peptide) bonds, usually a polymer of α-amino acids in which the α-carboxyl group of each amino acid residue is linked to the α-amino group of the next residue in a linear chain. The terms peptide, polypeptide and poly(amino acid) are used synonymously herein to refer to this class of compounds without restriction as to size. The largest members of this class are referred to as proteins.

A "label," "detector molecule," or "tracer" is any molecule which produces, or can be induced to produce, a detectable signal. The label can be conjugated to an analyte, immunogen, antibody, or to another molecule such as a receptor or a molecule that can bind to a receptor such as a ligand, particularly a hapten. Non-limiting examples of labels include radioactive isotopes, enzymes, enzyme fragments, enzyme substrates, enzyme inhibitors, coenzymes, catalysts, fluorophores, dyes, chemiluminescers, luminescers, or sensitizers; a non-magnetic or magnetic particle, a solid support, a liposome, a ligand, or a receptor.

The term "antibody" refers to a specific protein binding partner for an antigen and is any substance, or group of substances, which has a specific binding affinity for an antigen to the exclusion of other substances. The generic term antibody subsumes polyclonal antibodies, monoclonal antibodies and antibody fragments.

The term "derivative" refers to a chemical compound or molecule made from a parent compound by one or more chemical reactions.

The term "carrier" refers to solid particles and/or polymeric polymers such as immunogenic polymers such as those mentioned above. Where the carrier is a solid particle, the solid particle may be bound, coated with or otherwise attached to the polymeric material which preferably is a polyamine polymer to provide one or more reactive sites for bonding to the terminal functional group X in the compounds of the formula III.

The term "reagent kit," or "test kit," refers to an assembly of materials that are used in performing an assay. The reagents can be provided in packaged combination in the same or in separate containers, depending on their cross-reactivities and stabilities, and in liquid or in lyophilized form. The amounts and proportions of reagents provided in the kit can be selected so as to provide optimum results for a particular application. A reagent kit embodying features of the present invention comprises antibodies specific for the compounds of formula I and formula II. The kit may further comprise ligands of the analyte and calibration and control materials. The reagents may remain in liquid form or may be lyophilized.

The phrase "calibration and control materials" refers to any standard or reference material containing a known amount of a drug to be measured. The concentration of drug is calculated by comparing the results obtained for the unknown specimen with the results obtained for the standard. This is commonly done by constructing a calibration curve.

The term "biological sample" includes, but is not limited to, any quantity of a substance from a living thing or formerly living thing. Such living things include, but are not limited to, humans, mice, monkeys, rats, rabbits, horses, and other animals. Such substances include, but are not limited to, blood, serum, plasma, urine, cells, organs, tissues, bone, bone marrow, lymph, lymph nodes, synovial tissue, chondrocytes, synovial macrophages, endothelial cells, and skin.

Reagents and Immunogens

In constructing an immunoassay, a conjugate of the compound of formula IV is constructed to compete with the compounds of formula I or formula II in the sample for binding sites on the antibodies. In the immunoassay of this invention, the reagents are conjugates of a carrier with the compound of formula IV. In the compound of formula IV the linker spacer constitutes the "—B—(Y)p-X'—" portion of this molecule. The linker X' and the spacer "—B—(Y)p-"— are conventional in preparing conjugates and immunogens. Any of the conventional spacer-linking groups utilized to prepare conjugates and immunogens for immunoassays can be utilized in the compound of formula IV. Such conventional linkers and spacers are disclosed in U.S. Pat. Nos. 5,501,987 and 5,101,015.

Among the preferred spacer groups are included the spacer groups hereinbefore mentioned. Particularly preferred spacing groups are groups such as alkylene containing from 1 to 10 carbon atoms,

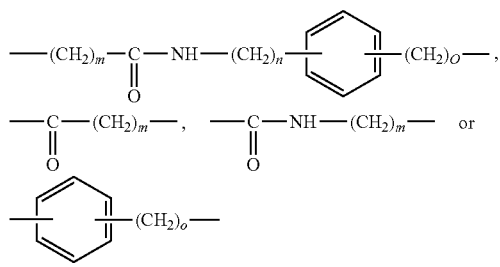

wherein m and o are integers from 0 to 6, and n is an integer from 1 to 6 with alkylene being the especially preferred spacing group In these formulae m is 0, n is preferably an integer of from 1-6, most preferably 1 or 2 and o is preferably 0 or 1.

In the compound of formula IV, X' is —$CH_2$— or a functional group linking the spacer to the carrier, preferably to an amine group on a polymeric carrier. The group X' is the result of the terminal functional group X in the compound of formula III which is capable of binding to a carrier, preferably to an amino group in the polyamine polymer present in the carrier or used as the immunogen. Any terminal functional group capable of binding to a carrier, preferably capable of reacting with an amine can be utilized as the functional group X in the compound of formula III. These terminal functional groups preferably included within X are:

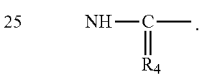

wherein $R_3$ is hydrogen or taken together with its attached oxygen atom forms a reactive ester and $R_4$ is oxygen or sulfur. The radical —N=C=$R_4$ can be an isocyanate or an isothiocyanate. The active esters formed by $OR_3$ include imidoester, such as N-hydroxysuccinamide, 1-hydroxy benzotriazole and p-nitrophenyl ester. However any active ester which can react with an amine group can be used.

The carboxylic group and the active esters are coupled to the carrier or immunogenic polymer by conventional means. The amine group on the polyamine polymer, such as a protein, produces an amide group which connects the spacer to the polymer, immunogens or carrier and/or conjugates of this invention. On the other hand, carriers can be coated with a polyamine polymer to supply the amino group for linking to the ligand portion.

In the immunogens and conjugates of the present invention, the chemical bonds between the carboxyl group-containing the compound of formula III as a hapten and the amino groups on the polyamine polymer on the carrier or immunogen can be produced using a variety of methods known to one skilled in the art. It is frequently preferable to form amide bonds. Amide bonds are formed by first activating the carboxylic acid moiety of the hapten in the compounds of formula III by reacting the carboxy group with a leaving group reagent (e.g., N-hydroxysuccinimide, 1-hydroxybenzotriazole, o- or p-nitrophenol, or o- or p-nitrophenyl chloroformate). An activating reagent such as dicyclohexylcarbodiimide, diisopropylcarbodiimide and the like can be used. The activated form of the carboxyl group in the hapten of formula III is then reacted with a buffered solution containing the protein carrier. Various methods of conjugating haptens and carriers are also disclosed in U.S. Pat. Nos. 3,996,344 and 4,016,146, which are herein incorporated by reference.

Where X is a terminal isocyanate or isothiocyanate radical in the compound of formula III, these radicals when reacted with the free amine of a polyamine polymer produce the conjugate or the immunogen of the hapten of formula IV where X' is,

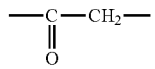

In the ligand of formula IV, X' functionally connects the hapten with the amino group on the polyamine containing carrier or on the immunogenic polypeptide.

Where X, in the compounds of formula III is an aldehyde group these compounds may be connected to the amine group of the polyamine polypeptide or carrier through an amine linkage by reductive amination. Any conventional method of condensing an aldehyde with an amine such as through reductive amination can be used to form this linkage. In this case, X' in the ligand portions of formula IV is —$CH_2$—. Any conventional means of condensing a reactive carbonyl with the amine group can be used in carrying out this condensation reaction.

The compound of formula III, when B is a methylene carbonyl of the formula:

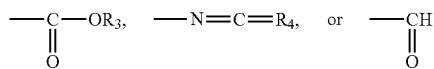

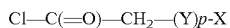

is produced by condensing the amine group in the compound of formula II with an acyl chloride of the formula:

Cl—C(=O)—$CH_2$—(Y)p-X      V

Any conventional method of reacting a primary amine with an acyl chloride can be used in this condensation procedure. Where Y is lower alkylene and B is the above methylene carbonyl group in the compound of formula III, this compound is produced by treating the compound of formula II with an anhydride of a di carboxylic acid such as glutaric anhydride. Any conventional means of condensing an anhydride with the primary amine group can be used in carrying out this condensation reaction The compound of formula III when B is —$CH_2$— may be produced by reacting the compound of formula I with an alkyl halide of the formula:

Halo $CH_2$—(Y)p-X      VII wherein Y, p and X are as above.

Any conventional means of condensing an alkyl halide with a primary amine group can be used in carrying out this condensation reaction.

The compound of formula III where B is —C(=O)—NH—CH$_2$ may be produced by condensing the compound of formula II with a halide or the formula:

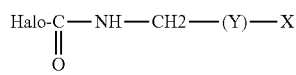

VIII wherein Y, p and X are as above.
utilizing conventional means.

The compound of formula III where B is —C(=O)—O—CH$_2$— may be produce by condensing the compound of formula II with a compound of the formula:

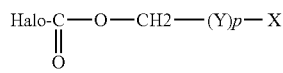

IX where Y, p and X are as above,
utilizing conventional means,

In cases where the compounds of formula V, VII, VIII, and IX contain a reactive amino group as well as a reactive carboxyl group, it is necessary to use an amine or ester protecting group during the reactions to form the compounds of formula III. Typically, the amines are protected by forming the corresponding N-trifluoroacetamide, N-tertbutyloxycarbonyl urethane (N-t-BOC urethane), N-carbobenzyloxy urethane or similar structure. Once the condensation reaction with the structure of formula I has been accomplished, as described above, the amine or the ester protecting group can be removed using reagents that do not otherwise alter the structure of the conjugate. Such reagents and methods are known to one skilled in the art and include weak or strong aqueous or anhydrous acids, weak or strong aqueous or anhydrous bases, hydride-containing reagents such as sodium borohydride or sodium cyanoborohydride and catalytic hydrogenation.

The compound of formula III can be converted into the immunogens and/or the conjugate reagents of this invention by reacting this compound with a carrier, preferably a polyamine polypeptide or a carrier coated with a polyamine polypeptide as described above. The same polypeptide can be utilized as the carrier and as the immunogenic polymer in the immunogen of this invention provided that polyamines or polypeptides are immunologically active. However, to form the conjugates used as reagents in the immunoassay, these polymers need not produce an immunological response as needed for the immunogens. In accordance with this invention, the various functional group represented by X in the compounds of formula III can be conjugated to the carrier by conventional means of attaching a functional group to a carrier. In accordance with a preferred embodiment, in the compounds of formula III, X is a carboxylic acid group or an activated carboxyl group.

Antibodies

The present invention also relates to novel antibodies, particularly monoclonal antibodies, to the compounds of formula I and formula II and mixtures thereof which can be produced by utilizing the aforementioned immunogens. It has been found that these antibodies produced in accordance with this invention are selectively reactive with the compounds of formula I and the compound of formula II and mixtures thereof. These antibodies do not react with non-pharmaceutically inactive metabolites of the compounds of formula I and the compound of formula II which would interfere with immunoassays for either the compound of formula I and the compound of formula II. The ability of the antibodies of this invention not to react with these inactive metabolites makes these antibodies particularly valuable in providing an immunoassay for either the compound of formula I or the compound of formula II.

The present invention relates to these selectively reactive novel antibodies to the compounds of formula I and formula II and mixtures thereof. The antisera of the invention can be conveniently produced by immunizing host animals with the immunogens of this invention. Suitable host animals include rodents, such as, for example, mice, rats, rabbits, guinea pigs and the like, or higher mammals such as goats, sheep, horses and the like. Initial doses, bleedings and booster shots can be given according to accepted protocols for eliciting immune responses in animals. Through periodic bleeding, the blood samples of the immunized mice were observed to develop an immune response against the compounds of formula I and II utilizing conventional immunoassays. These methods provide a convenient way to screen for hosts and antibodies which are producing antisera having the desired activity.

The antibodies having substantially 100% selective reactivity with lenalidomide and substantially no selective reactivity with thalidomide or substantially selective reactivity with both thalidomide and lenalidomide can be produced utilizing the immunogen of formula III and by the screening method disclosed below. This screening method can be used to obtain antibodies which are reactive with both the lenalidomide and thalidomide chemotherapeutic agents, antibodies which are specific and selective to lenalidomide and antibodies having any desired relative reactivity with regard to these chemotherapeutic agents.

In preparing these antibodies, an immunogenic carrier can be conjugated with the immunogen of formula III and used to immunize host animals such as mice, rabbits, sheep or rats. Development of the immune response to the compound of formula III can be monitored by ELISA utilizing microtiter plates coated with a conjugate of BSA and the compound of formula III. Once the immune response has been sufficiently developed the spleen cells of the host animal can be isolated and fused with an immortalized cell line. With respect to producing monoclonal antibodies the fused cells can be plated on 96-well plates and grown in the presence of a selective medium to select hybridoma cells. Hybridoma supernatants and antisera can be assayed for the presence of anti-lenalidomide antibodies by ELISA. Antibodies from wells that gave positive ELISA results can be tested for lenalidomide and thalidomide binding by indirect competitive microtiter plate assay. The IC$_{50}$ values of an analyte such as lenalidomide and thalidomide and their metabolites, can be calculated from this assay. The IC$_{50}$ (inhibitory concentration at 50%) of an analyte in an assay is the concentration of that analyte in a sample at which the signal in the assay is 50% of the total signal for the assay in the absence of analyte in an inhibition assay. -Selective reactivity of an analyte is calculated from a ratio of the IC$_{50}$'s expressed as a %:100%−[IC$_{50}$-analyte/(IC$^I_{50}$-lenalidomide+IC$^I_{50}$-thalidomide)]×100. For antibodies having substantially 100% selective reactivity with lenalidomide and substantially no selective reactivity with thalidomide this value will approach 100%. The calculation of the IC$_{50}$ is carried out according to the procedure found in The Immunoassay Handbook, pp 108-110, 3rd edition, edited by D. Wild, published by Elsevier, Amsterdam, 2005. As seen from the above formula, the $IC_{50}$ of an analyte is inversely proportional to the reactivity of the analyte. Cells from wells that had desired relative reactivity with both lenalidomide and thalidomide can be obtained by screening and sub-cloning by limiting dilution to isolate individual clones producing monoclonal antibodies having the desired reactivity with thalidomide and lenalidomide Monoclonal antibodies are produced conveniently by immunizing Balb/c mice according to the schedule followed by injecting the mice with additional immunogen i.p. or i.v. on three successive days starting three days prior to the cell fusion. Other protocols well known in the antibody art may of course be utilized as well. The complete immunization protocol detailed herein provided an optimum protocol for serum antibody response for the antibody to the compounds of formula I and II.

B lymphocytes obtained from the spleen, peripheral blood, lymph nodes or other tissue of the host may be used as the monoclonal antibody producing cell. Most preferred are B lymphocytes obtained from the spleen. Hybridomas capable of generating the desired monoclonal antibodies of the invention are obtained by fusing such B lymphocytes with an immortal cell line, which is a cell line that imparts long term tissue culture stability on the hybrid cell. In the preferred embodiment of the invention the immortal cell may be a lymphoblastoid cell or a plasmacytoma cell such as a myeloma cell. Murine hybridomas which produce lenalidomide and thalidomide monoclonal antibodies are formed by the fusion of mouse myeloma cells and spleen cells from mice immunized with the aforementioned immunogenic conjugates. Chimeric and humanized monoclonal antibodies can be produced by cloning the antibody expressing genes from the hybridoma cells and employing recombinant DNA methods now well known in the art to either join the subsequence of the mouse variable region to human constant regions or to combine human framework regions with complementary determining regions (CDR's) from a donor mouse or rat immunoglobulin. An improved method for carrying out humanization of murine monoclonal antibodies which provides antibodies of enhanced affinities is set forth in International Patent Application WO 92/11018.

Polypeptide fragments comprising only a portion of the primary antibody structure may be produced, which fragments possess one or more immunoglobulin activities. These polypeptide fragments may be produced by proteolytic cleavage of intact antibodies by methods well known in the art, or by inserting stop codons at the desired locations in expression vectors containing the antibody genes using site-directed mutageneses to produce Fab fragments or (Fab')2 fragments. Single chain antibodies may be produced by joining VL and VH regions with a DNA linker (see Huston et al., *Proc. Natl. Acad. Sci. U.S.A.*, 85:5879-5883 (1988) and Bird et al., *Science*, 242:423-426 (1988))

The antibodies produced in accordance with this invention can be selectively reactive with the compound of formula II or both the compounds of formula I and the compound of formula II without having any substantial cross-reactivity with the pharmacologically, therapeutically non-active metabolites of the compound of formula I and the compound of formula II. By having no substantial cross-reactivity, it is meant that the antibodies of this invention have cross-reactivity relative to both their reactivity with the compound of formula I and the compound of formula II of less than 10%, preferably less than 5%.

In accordance with this invention antibodies which are selectively reactive with lenalidomide and have no selective reactivity with thalidomide can be produced. By an antibody having selective reactivity for lenalidomide and with no selective reactivity with thalidomide, it is meant that the antibody has at least 95% activity for lenalidomide based upon its reactivity or binding with both thalidomide and lenalidomide. In order to be utilized in a thalidomide immunoassay the antibody should be selectively reactive with both lenalidomide and thalidomide and have a cross-reactivity with the aforementioned pharmacologically, therapeutically non-active metabolites of the compound of formula I and the compound of formula II of less than 10% based upon its reactivity with the both the compounds of formula I and formula II and have a reactivity with thalidomide of at least 10% based upon its reactivity with both thalidomide and lenalidomide. In order to be utilized in a lenalidomide immunoassay, any antibody of this invention which is selectively reactive with lenalidomide or is selectively reactive with both lenalidomide and thalidomide and have a cross-reactivity with the aforementioned pharmacologically, therapeutically non-active metabolites of the compound of formula I and the compound of formula II of less than 10% based upon its reactivity with the both the compounds of formula I and formula II can be used.

Immunoassays

In accordance with this invention, the conjugates and the antibodies generated from the immunogens of the compound of formula III can be utilized as reagents for the determination of the compounds of formula I and formula II in patient samples. This determination is performed by means of an immunoassay. Any immunoassay in which the reagent conjugates formed from the compound of formula III compete with the compound of formula I or formula II in the sample for binding sites on the antibodies generated in accordance with this invention can be utilized to determine the presence of the compound of formula I or formula II in a patient sample. The manner for conducting such an assay for the compound of formula I and formula II in a sample suspected of containing lenalidomide or thalidomide, comprises combining an (a) aqueous medium sample, (b) an antibody to the compound of formula I and formula II generated in accordance with this invention and (c) the conjugates formed from the compound of formula III. The compound of formula I or formula II in the sample can be determined by measuring the inhibition of the binding to the specific antibody of a known amount of the conjugate added to the mixture of the sample and antibody. The result of the inhibition of such binding of the known amount of conjugates by the unknown sample is compared to the results obtained in the same assay by utilizing known standard solutions of the compounds of formula I or formula II. In determining the amount of the compounds of formula I or formula II in an unknown sample, the sample, the conjugates formed from the compounds of formula III and the antibody may be added in any order.

Various means can be utilized to measure the amount of conjugate formed from the compound of formula III bound to the antibody. One method is where binding of the conjugates to the antibody causes a decrease in the rate of rotation of a fluorophore conjugate. The amount of decrease in the rate of rotation of a fluorophore conjugate in the liquid mixture can be detected by the fluorescent polarization technique such as disclosed in U.S. Pat. Nos. 4,269,511 and 4,420,568.

On the other hand, the antibody can be coated or absorbed on nanoparticles so that when these particles react with the compounds of formula I or formula II and conjugates formed from the compounds of formula III these nanoparticles form an aggregate. However, when the antibody coated or absorbed on nanoparticles react with thalidomide or lenalidomide in the sample, the thalidomide or lenalidomide from the sample bound to these nanoparticles does not cause aggregation of the antibody nanoparticles. The amount of aggregation or agglutination can be measured in the assay mixture by absorbance.

On the other hand, these assays can be carried out by having either the antibody or the compounds of formula III attached to a solid support such as a microtiter plate or any other conventional solid support including solid particles. Attaching antibodies and proteins to such solid particles is well known in the art. Any conventional method can be utilized for carrying out such attachments. In many cases, in order to aid measurement, labels may be placed upon the antibodies, conjugates or solid particles, such as radioactive labels or enzyme labels, as aids in detecting the amount of the conjugates formed from the compound of formula III which is bound or unbound with the antibody. Other suitable labels include chromophores, fluorophores, etc.

As a matter of convenience, assay components of the present invention can be provided in a kit, a packaged combination with predetermined amounts of new reagents employed in assaying for the compounds of formula I or formula II. These reagents include the antibody of this invention, as well as, the conjugate formed from the compounds of formula III. In carrying out an immunoassay in accordance with this invention the radicals p, X, Y and B in the reagent and the immunogen which forms the antibody used in a given immunoassay can be the same or be a different substituent within the groups defined for each of these radicals. Therefore while the definitions of the radicals p, X, Y, and B are the same for the conjugate reagent and the immunogen, the particular substituent which these radicals represent for the immunogen and the conjugate reagent in a given assay may be different.

In addition to these necessary reagents, additives such as ancillary reagents may be included, for example, stabilizers, buffers and the like. The relative amounts of the various reagents may vary widely to provide for concentrations in solution of the reagents which substantially optimize the sensitivity of the assay. Reagents can be provided in solution or as a dry powder, usually lyophilized, including excipients which on dissolution will provide for a reagent solution having the appropriate concentrations for performing the assay.

EXAMPLES

In the examples, the following abbreviations are used for designating the following:

| | |
|---|---|
| HATU | O-(7-Azabenzotriazol-1-yl)-N,N,N',N'-tetramethyluronium hexafluorophosphate |
| DIPEA | N-N'-Diisopropylethylamine |
| DMF | Dimethylformamide |
| TFA | Trifluoroacteic acid |
| CH$_2$Cl$_2$ | dicholoromethane |
| DMSO | Dimethylsulfoxide |
| NHS | N-hydroxy succinimide |
| s-NHS | sulfo-N-hydroxy succinimide |
| EDC | 1-(3-dimethylaminopropyl)-3-ethylcarbodiimide hydrochloride |
| KLH | Keyhole Limpet Hemocyanin |
| BSA | Bovine serum albumin |
| PBS | Phosphate buffered saline |
| NaCl | sodium chloride |

-continued

| | |
|---|---|
| HRP | horseradish peroxidase |
| ANS | 8-Anilino-1-naphthalenesulfonic acid |
| TMB | 3,3',5,5'-Tetramethylbenzidine |
| TRIS | Tris(hydroxymethyl)aminomethane hydrochloride |
| di H$_2$O | deionized water |

The phosphate buffer composition has an aqueous solution containing 15.4 mM Sodium phosphate dibasic (Na$_2$HPO$_4$)

4.6 mM Sodium phosphate monobasic (NaH$_2$PO$_4$)

pH=7.2±0.10

In the examples, Schemes 1-2 below set forth the specific compounds prepared and referred to by numbers in the Examples. The schemes are as follows:

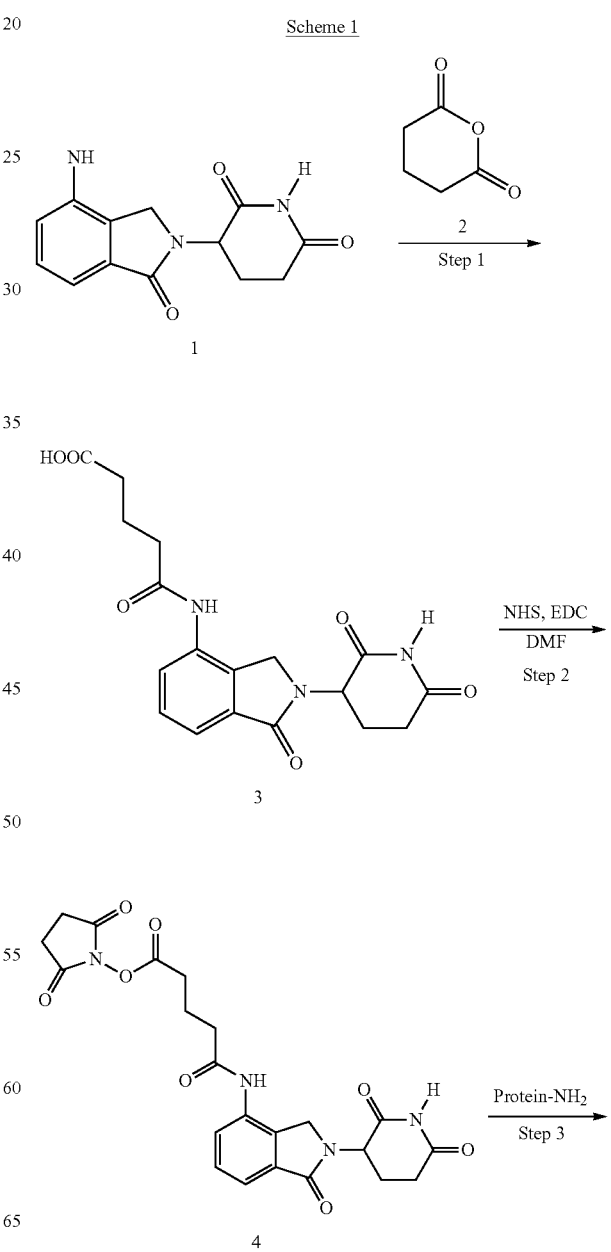

17
-continued

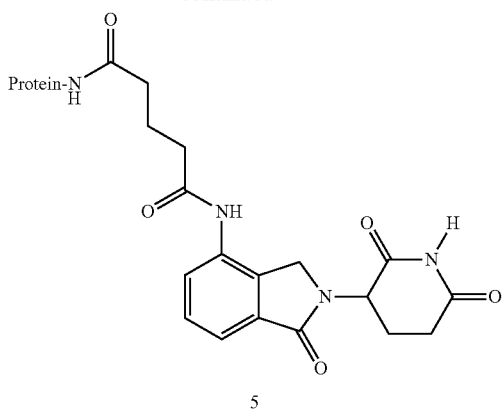

5

Scheme 2

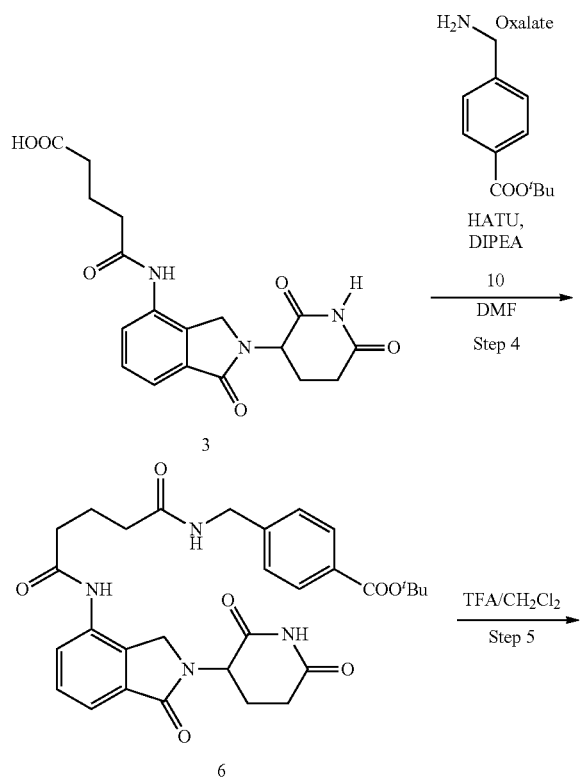

18
-continued

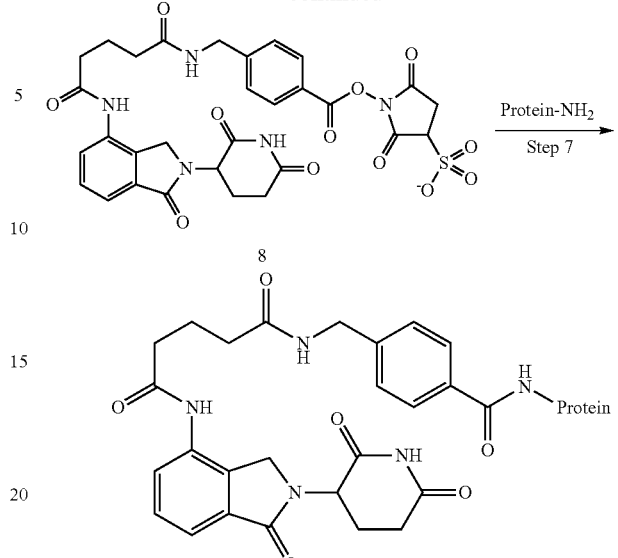

Example 1

Preparation of Carbamoyl Pentantoic Acid Derivative of Lenalidomide Derivative [3](Scheme 1)

A mixture of lenalidomide [1] (1.0 g, 3.86 mmol) and glutaric anhydride [2] (0.48 g, 4.25 mmol) in anhydrous toluene was heated and refluxed under nitrogen for 3.5 hours. Another portion of glutaric anhydride [2] (0.18 g, 1.53 mmol) was added and the mixture was heated another 2 hours to produce [3]. The mixture was cooled to 0° C., to precipitate [3]. The precipitated solid was filtered, and washed with $CH_2Cl_2$ to obtain 1.55 g of crude compound [3]. This crude compound was recrystallized from ethanol (20 mL)/$H_2O$ (1 mL) to obtain pure [3] (1.30 g, 90%) as a white solid.

Example 2

Preparation of carbamoyl-butyrylamino-methyl Benzoic Acid Derivative of Lenalidomide Derivative [7] (Scheme 2)

The compound [3] produced in example 1 (800 mg, 2.14 mmol) was dissolved in anhydrous DMF (20 mL) under nitrogen, to which was added diisopropylethyl amine (DIPEA) (1.27 mL, 7.27 mmol) and the amine [10] (700 mg, 2.35 mmol) followed by HATU (1.88 g, 4.93 mmol). This reaction mixture was stirred at 25° C. for 24 hours to produce [6]. The contents of the flask were diluted with ethyl acetate. The organic phase (ethyl acetate) was washed with 1 M hydrochloric acid, saturated sodium bicarbonate and water. The ethylacetate layer was then dried over sodium sulfate, which was filtered off. Removal of the ethylacetate solvent provided the crude product [6], which was purified by flash chromatography with 100% EtOAc and 1-2% MeOH/EtOAc to obtain the pure product [6] (680 mg, 57%) as a white solid.

$^1$H NMR (300 MHz, DMSO-$d_6$): δ 11.03 (s, 1H), 9.82 (s, 1H), 8.46 (t, J=6.0 Hz, 1H), 7.82-7.86 (m, 3H), 7.46-7.52 (m, 2H), 7.35 (d, J=8.3 Hz, 2H), 5.14 (dd, J=5.0, 13.5 Hz, 1H), 4.32-4.38 (m, 4H), 2.86-2.96 (m, 1H), 2.56-2.64 (m, 2H), 2.39 (t, J=7.5 Hz, 2H), 2.25 (t, J=7.5 Hz, 2H), 1.97-2.05 (m, 1H), 1.82-1.92 (m, 2H), 1.53 (s, 9H). APCI]$^-$=561.

This white solid [6] (676 mg, 1.20 mmol) was dissolved in dichloromethane (3 mL). To this solution of compound [6] at 0° C. under N$_2$ was added TFA (3 mL) to produce [7]. The dichloromethane was removed under reduced pressure and the resulting residue [7]was triturated with ether to isolate the crude acid. This material was recrystallized from aqueous EtOH to obtain pure [7] (507 mg, 83%).

Example 3

General Method for Preparing NHS/S-NHS Activated Drug Derivatives from the Corresponding Acids [3] & [7]

Lenalidomide acid derivative [3] was activated with EDC and NHS to produce the NHS activated ester of lenalidomide [4] for eventual conjugation to proteins (examples 4 and 5a). Lenalidomide acid derivative [7] was activated with EDC and s-NHS to produce the s-NHS activated ester of lenalidomide [8] for eventual conjugation to protein (example 5b).

Example 3a

Preparation of NHS Activated Ester Lenalidomide Carbamoyl Pentanoic Acid Derivative [4]

Lenalidomide derivative [3], example 1, scheme 1, (67.62 mg) was dissolved in 7 mL of DMSO to which was added NHS (590.60 mg) and EDC (93.00 mg). The reaction mixture was stirred for 20 hours at ambient temperature under a nitrogen atmosphere to produce the NHS activated ester of lenalidomide derivative [4]. The reaction mixture was used directly in examples 4 and 5a.

Example 3b

Preparation of S-NHS Activated Ester Lenalidomide carbamoyl-butyrylamino-methyl Benzoic Acid Derivative [8]

Lenalidomide derivative [7], example 2, scheme 2 (16.3 mg) was dissolved in 1.6 mL of DMSO to which was added s-NHS (25.3 mg) and EDC (18.1 mg). The reaction mixture was stirred for 20 hours at ambient temperature under a nitrogen atmosphere to produce the s-NHS activated ester of lenalidomide derivative [8]. The reaction mixture was used directly in example 5b.

Example 4

Preparation of KLH Immunogen with Activated Hapten [4]

A protein solution of KLH was prepared by dissolving 300 mg of KLH in 15 mL of phosphate buffer (50 mM, pH 7.5), followed by addition of 1.5 mL DMSO and 3.50 mL of NHS activated lenalidomide derivative [4] prepared in Example 3a. The reaction mixture of KLH and activated lenalidomide derivative [4] was allowed to stir for 20 hours at room temperature to produce the lenalidomide-KLH conjugate [5]. The lenalidomide-KLH conjugate [5] was then purified by dialysis against 10% DMSO in phosphate buffer (50 mM, pH 7.5) at room temperature. Thereafter lenalidomide-KLH conjugate [5] was dialyzed against phosphate buffer (50 mM, pH 7.5) at room temperature. The last dialysis was performed against phosphate buffer at 4° C. The lenalidomide-KLH conjugate [5] was characterized by ultraviolet-visible spectroscopy (UV/VIS). The conjugate was diluted to a final concentration of 2 mg/mL in phosphate buffer (50 mM, pH 7.5).

Example 5a

Preparation of BSA Conjugate with Activated Hapten [4]

A protein solution of BSA was prepared by dissolving 1 g BSA in phosphate buffer (50 mM, pH 7.5) for a final concentration of 50 mg/mL. DMSO (3.3 mL) was slowly added to the protein solution of BSA while stirring on ice, followed by addition of 0.60 mL of NHS activated lenalidomide derivative [4] prepared in Example 3a. The amount of NHS activated lenalidomide derivative [4] added to the protein solution of BSA was calculated for a 1:1 molar ratio between the derivative of lenalidomide [4] and BSA. The mixture of BSA and activated lenalidomide derivative [4] was allowed to stir for 18 hours at room temperature to produce the conjugate of the activated lenalidomide ester [4] and BSA. This conjugate was then purified by dialysis against 10% DMSO in phosphate buffer (50 mM, pH 7.5) at room temperature. Thereafter lenalidomide-BSA conjugate [5] was dialyzed against phosphate buffer (50 mM, pH 7.5) at room temperature. The last dialysis was performed against phosphate buffer at 4° C. The purified lenalidomide-BSA conjugate [5] was characterized by UV/VIS spectroscopy.

Example 5b

Preparation of BSA Conjugate with Activated Hapten [8]

A protein solution of BSA was prepared by dissolving 0.5 g BSA in phosphate buffer (50 mM, pH 7.5) for a final concentration of 50 mg/mL. s-NHS activated lenalidomide derivative [8] prepared in Example 3b was slowly added to the protein solution of BSA while stirring on ice. The amount of s-NHS activated lenalidomide derivative [8] added to the protein solution of BSA was calculated for a 1:1 molar ratio between the derivative of lenalidomide [8] and BSA. The mixture of BSA and activated lenalidomide derivative [8] was allowed to stir for 18 hours at room temperature to produce the conjugate of the activated lenalidomide ester [8] and BSA. This conjugate was then purified by dialysis against 10% DMSO in phosphate buffer (50 mM, pH 7.5) at room temperature. Thereafter lenalidomide-BSA conjugate [9] was dialyzed against phosphate buffer (50 mM, pH 7.5) at room temperature. The last dialysis was performed against phosphate buffer at 4° C. The purified lenalidomide-BSA conjugate [9] was characterized by UV/VIS spectroscopy.

Example 6a

Preparation of Polyclonal Antibodies to Lenalidomide [3]

Ten female BALB/c mice were immunized i.p. with 100 µg/mouse of lenalidomide-KLH immunogen [5], as prepared in Example 4, emulsified in Complete Freund's adjuvant. The mice were boosted once, four weeks after the initial injection with 100 µg/mouse of the same immunogen emulsified in Incomplete Freund's Adjuvant. Twenty days after the boost, test bleeds containing polyclonal antibodies from each mouse were obtained by orbital bleed. The anti-serum from these test bleeds containing lenalidomide antibodies were evaluated in Examples 8 and 9.

Example 6b

Preparation of Monoclonal Antibodies to Lenalidomide [3]

Mice from Example 6a that were immunized with lenalidomide-KLH conjugate [5] prepared in Example 4 were used to produce monoclonal antibodies. For monoclonal antibodies starting three days before the fusion, the mice were injected i.p. with 400 µg (3 days before fusion), 200 µg (2 days before fusion), and 200 µg (1 day before fusion) of lenalidomide-KLH conjugate [5] in PBS prepared in Example 4. Spleen cells were isolated from the selected mice and fused with $2 \times 10^7$ SP2/0 cells with 50% polyethylene glycol 1500 according to the method of Coligan, J. E. et al., eds., *Current Protocols in Immunology*, 2.5.1-2.5.8, (1992), Wiley & Sons, NY. The fused cells were plated on ten 96-well plates in DMEM/F12 supplemented with 20% FetalClone I, 2% L-glutamine (100 mM) and 2% 50×HAT. Two to three weeks later, the hybridoma supernatant was assayed for the presence of anti-lenalidomide antibodies by ELISA (as in example 8b). Cells from the wells that gave positive ELISA results were expanded to 24 well plates. These monoclonal antibodies were tested for lenalidomide and thalidomide binding by indirect competitive microtiter plate assay as described in example 9. Clones positive by ELISA were subcloned at least once by limiting dilution according to the method disclosed in Coligan, J. E. et al., eds., *Current Protocols in Immunology*, 2.5.8-2.5.17, (1992), Wiley & Sons, NY.

Example 7a

Microtiter Plate Sensitization Procedure with Lenalidomide-BSA Conjugate [5]

The ELISA method for measuring lenalidomide concentrations was performed in polystyrene microtiter plates (Nunc MaxiSorp F8 Immunomodules) optimized for protein binding and containing 96 wells per plate. Each well was coated with lenalidomide-BSA conjugate [5] (prepared as in Example 5a) by adding 300 µL of lenalidomide-BSA conjugate [5] at 10 µg/mL in 0.05M sodium carbonate, pH 9.6, and incubating for three hours at room temperature. The wells were washed with 0.05M sodium carbonate, pH 9.6 and then were blocked with 375 µL of 5% sucrose, 0.2% sodium caseinate solution for 30 minutes at room temperature. After removal of the post-coat solution the plates were dried at 37° C. overnight.

Example 7b

Microtiter Plate Sensitization Procedure with Lenalidomide-BSA Conjugate [9]

The ELISA method for measuring lenalidomide concentrations was performed in polystyrene microtiter plates (Nunc MaxiSorp F8 Immunomodules) optimized for protein binding and containing 96 wells per plate. Each well was coated with lenalidomide-BSA conjugate [9] (prepared as in Example 5b) by adding 300 µL of lenalidomide-BSA conjugate [9] at 10 µg/mL in 0.05M sodium carbonate, pH 9.6, and incubating for three hours at room temperature. The wells were washed with 0.05M sodium carbonate, pH 9.6 and then were blocked with 375 µL of 5% sucrose, 0.2% sodium caseinate solution for 30 minutes at room temperature. After removal of the post-coat solution the plates were dried at 37° C. overnight.

Example 8a

Antibody Screening Procedure—Titer

This procedure is to find the dilution of antibody to be tested for displacement as in Example 9. The ELISA method for screening lenalidomide antibodies (produced in Example 6) was performed with the microtiter plates that were sensitized with lenalidomide-BSA conjugates prepared in Examples 7a and 7b. The antibody screening assay was performed by diluting the murine serum from test bleeds (as in Example 6a) containing polyclonal lenalidomide antibodies to 1:2,000, 1:6,000, 1:18,000 and 1:54,000 (volume/volume) in phosphate buffered saline containing 0.1% BSA and 0.01% thimerosal. To each well of lenalidomide-BSA sensitized wells (prepared in Examples 7a and 7b) 50 µL phosphate buffered saline containing 0.1% BSA and 0.01% thimerosal and 50 µL of diluted antibody were added and incubated for 10 minutes at room temperature with shaking. During this incubation antibody binds to the lenalidomide-BSA conjugate passively absorbed in the wells (Examples 7a and 7b). The wells of the plates were washed three times with 0.02 M TRIS, 0.9% NaCl, 0.5% Tween-80 and 0.001% thimerosal, pH 7.8 to remove any unbound antibody. To detect the amount of lenalidomide antibody bound to the lenalidomide-BSA conjugate in the wells, 100 µL of a goat anti-mouse antibody—HRP enzyme conjugate (Jackson Immunoresearch) diluted to a specific activity (approximately 1/3000) in PBS with 0.1% BSA, 0.05% ANS, 0.01% thimerosal, capable of binding specifically with murine immunoglobulins and producing a colored product when incubated with a substrate, in this example TMB, were added to each well. After an incubation of 10 minutes at room temperature with shaking, during which the goat anti-mouse antibody—HRP enzyme conjugate binds to lenalidomide antibodies in the wells, the plates were again washed three times to remove unbound goat anti-mouse antibody—HRP enzyme conjugate. To develop a measurable color in the wells washing was followed by the addition of 100 µL of TMB (TMB Substrate, BioFx), the substrate for HRP, to develop color during a 10 minute incubation with shaking at room temperature. Following the incubation for color development, 50 µL of stop solution (1.5% sodium fluoride in di $H_2O$) was added to each well to stop the color development and after 20 seconds of shaking the absorbance was determined at 650 nm (Molecular Devices Plate Reader). The amount of antibody in a well was proportional to the absorbance measured and was expressed as the dilution (titer) resulting in an absorbance of 1.5. Titers were determined by graphing antibody dilution of the antibody measured (x-axis) vs. absorbance 650 nm (y-axis) and interpolating the titer at an absorbance of 1.5. The titer which produced absorbance of 1.5 determined the concentration (dilution) of antibody used in the indirect competitive microtiter plate assay described in Example 9.

Example 8b

Antibody Screening Procedure—Monoclonal Screening

The ELISA method for screening lenalidomide monoclonal antibodies (produced in example 8b) was performed with the microtiter plates that were sensitized with lenalidomide-BSA conjugate [9] as described in example 7b. To each well of lenalidomide-BSA sensitized wells (prepared in example 7b) 50 µL phosphate buffered saline containing 0.1% BSA and 0.01% thimerosal and then 50 µL of monoclonal culture supernatant were added and incubated for 10 minutes at room temperature with shaking. During this incubation antibody binds to the lenalidomide-BSA conjugate in the well. The wells of the plates were washed three times with 0.02 M TRIS, 0.9% NaCl, 0.5% Tween-80 and 0.001% thimerosal, pH 7.8 to remove any unbound antibody. To detect the amount of lenalidomide antibody bound to the lenalidomide-BSA conjugate in the wells, 100 µL of a goat anti-mouse antibody—HRP enzyme conjugate (Jackson Immunoresearch) diluted 1/3000 in PBS with 0.1% BSA, 0.05% ANS, 0.01% thimerosal, capable of binding specifically with murine immunoglobulins and producing a colored product when incubated with a substrate, in this example TMB, were added to each well. After an incubation of 10 minutes at room temperature with shaking, during which the goat anti-mouse antibody—HRP enzyme conjugate binds to lenalidomide antibodies in the wells, the plates were again washed three times to remove unbound goat anti-mouse antibody—HRP enzyme conjugate. To develop a measurable color in the wells washing was followed by the addition of 100 µL of TMB (TMB Substrate, BioFx), the substrate for HRP, to develop color during a 10 minute incubation with shaking at room temperature. Following the incubation for color development, 50 µL of stop solution (1.5% sodium fluoride in diH$_2$O) was added to each well to stop the color development and after 10 seconds of shaking the absorbance was determined at 650 nm (Molecular Devices Plate Reader). The amount of antibody in a well was proportional to the absorbance measured. Samples with an absorbance of greater than three or more times background were designated as positive. Samples with absorbance above 0.4 or fifty samples with highest absorbance were expanded to 24 well plates, as described in Example 8b.

Example 9

Indirect Competitive Microtiter Plate Immunoassay Procedure Determining IC$_{50}$ for Antibodies to Lenalidomide The ELISA method for determining IC$_{50}$ values was performed with the microtiter plates that were sensitized with lenalidomide-BSA conjugate [9] as described in Example 7b. The analytes—lenalidomide and thalidomide were dissolved in DMSO and diluted in diH$_2$O over a concentration range of 1 to 100,000 ng/mL. Each of the assays were performed by incubating 50 µL of the analyte solution with 50 µL of one of the antibodies selected from the polyclonal antibodies produced in Example 6a with the immunogen of Example 4 (lenalidomide) and the monoclonal antibody produced in Example 8b (lenalidomide and thalidomide). The assays were all performed by diluting the concentration of the antibodies in each of the wells to the titer determined in Example 8a. During the 10 minute incubation (at room temperature with shaking) there is a competition of antibody binding for the lenalidomide-BSA conjugate in the well (produced in Example 7b) and the analyte in solution. Following this incubation the wells of the plate were washed three times with 0.02 M TRIS, 0.9% NaCl, 0.5% Tween-80 and 0.001% thimerosal, pH 7.8 to remove any material that was not bound. To detect the amount of lenalidomide antibody bound to the lenalidomide-BSA conjugate in the wells (produced in Example 7b), 100 µL of a goat anti-mouse antibody—HRP enzyme conjugate (Jackson Immunoresearch) diluted to a predetermined specific activity (approximately 1/3000) in PBS with 0.1% BSA, 0.05% ANS, 0.01% thimerosal, capable of binding specifically with murine immunoglobulins and producing a colored product when incubated with a substrate, in this example TMB, were added to each well. After an incubation of 10 minutes at room temperature with shaking, during which the goat anti-mouse antibody—HRP enzyme conjugate binds to lenalidomide antibodies in the wells, the plates were again washed three times to remove unbound secondary conjugate. To develop a measurable color in the wells washing was followed by the addition of 100 µL of TMB (TMB Substrate, BioFx), the substrate for HRP, to develop color in a 10 minute incubation with shaking at room temperature. Following the incubation for color development, 50 µL of stop solution (1.5% sodium fluoride in di H$_2$O) was added to each well to stop the color development and after 20 seconds of shaking the absorbance was determined at 650 nm (Molecular Devices Plate Reader). The amount of antibody in a well was proportional to the absorbance measured and inversely proportional to the amount of lenalidomide or thalidomide in the sample. The IC$_{50}$'s of lenalidomide and thalidomide were determined by constructing dose-response curves with the absorbance in the wells plotted versus analyte concentration in the wells. The absorbance of the color in the wells containing analyte was compared to that with no analyte and a standard curve was generated. The IC$_{50}$ value for a given analyte was defined as the concentration of analyte that was required to have 50% of the absorbance of the wells containing no analyte. Results for polyclonal antibodies to lenalidomide are in table I below. Results for monoclonal antibodies to lenalidomide are in table II below.

TABLE I

IC$_{50}$'s of lenalidomide and titers of polyclonal antibodies to lenalidomide (Example 6a) using plates coated with lenalidomide-BSA conjugate [9] (Example 7b).

| Bleed # | Titer | IC$_{50}$, ng/mL |
|---|---|---|
| 1 | 51,000 | 84 |
| 2 | 66,000 | 59 |
| 3 | 28,000 | 3,400 |
| 4 | 15,000 | 2,200 |
| 5 | 111,000 | 510 |
| 6 | 5,200 | 810 |
| 7 | 9,300 | 80 |
| 8 | 9,400 | 870 |
| 9 | 58,000 | 570 |
| 10 | 18,000 | 9 |

TABLE II

IC$_{50}$'s of lenalidomide and thalidomide using monoclonal antibodies to lenalidomide (Example 6b) using plates coated with lenalidomide-BSA conjugate [9] (Example 7b).

| Monoclonal antibody number | Analyte | | % cross-reactivity to Thalidomide |
|---|---|---|---|
| | Lenalidomide | Thalidomide | |
| 1H12 | 1 | 7 | <15% |
| 6G1 | 11 | 992 | <2% |
| 7E4 | 6 | 7 | <86% |

As seen from these tables, the antibodies of this invention are substantially reactive with lenalidomide and thalidomide.

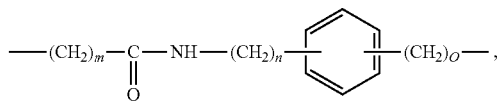

-continued
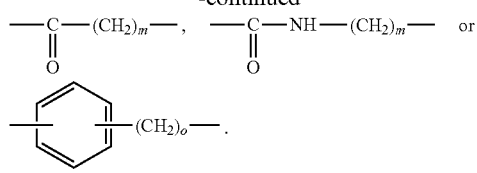
19. The kit of claim 18, wherein Y is
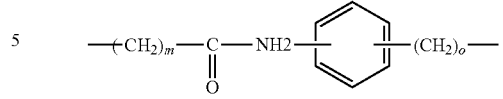

What is claimed:

1. An Immunoassay for detecting thalidomide in a sample comprising providing a mixture containing said sample, an antibody being selectively reactive with mixture of the pharmaceutically active chemotherapeutic drugs lenalidomide and thalidomide and having a reactivity with thalidomide of at least 10% based upon its reactivity with said mixture of pharmaceutically active chemotherapeutic drugs and a conjugate of a carrier with a ligand having the formula:

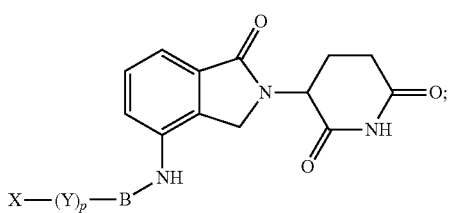

wherein B is —C(=O)—CH2-, —C(=O)—NH—CH2-, —C(=O)—O—CH2- or —CH2-
Y is an organic spacing group;
p is an integer from 0 to 1; and
X is a terminal functional group capable of binding to a carrier;
causing the thalidomide in said sample and said conjugate to bind with said antibody and thereafter measuring the said conjugate in said mixture that is bond or unbound to said antibody, whereby the presence of thalidomide in said sample can be detected.

2. The immunoassay of claim 1 wherein the sample is a human sample.

3. The immunoassay of claim 2 wherein said human sample is a sample taken from a patient treated with thalidomide and said immunoassay measures the amount of thalidomide in the sample by measuring the amount of conjugate which is bound or unbound to said antibody.

4. The immunoassay of claim 1 wherein said antibody of has a cross reactivity with the non-pharmaceutically active metabolites of said pharmaceutically active chemotherapeutic drugs of not greater than 10%, said cross-reactivity being relative to said antibody's binding to said mixture of pharmaceutically active chemotherapeutic drugs.

5. The immunoassay of claim 4 wherein said antibody is generated from an immunogen comprising an immunogenic carrier containing polyamine polymer conjugated with a ligand of the formula:

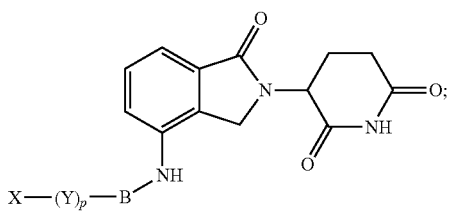

wherein Y and B are as above and X is a terminal functional group capable of binding to said polyamine polymer.

6. The immunoassay of claim 5, wherein the antibody is attached to a solid support.

7. The immunoassay of claim 6, wherein the solid support is microtitor plates.

8. The immunoassay of claim 6, wherein the solid support is nanoparticles.

9. The immunoassay of claim 1, wherein said antibody is a monoclonal antibody.

10. The immunoassay of claim 9, wherein said antibody is derived from mice, rabbits, sheep or rats.

11. The immunoassay of claim 4 wherein said antibody is a monoclonal antibody.

12. The immunoassay of claim 4 wherein said antibody has reactivity with thalidomide of at least 40% based upon its reactivity with said mixture of chemotherapeutic drugs.

13. A kit for determining the presence of thalidomide in a patient sample comprising separate reagents packaged in separate containers, one of said reagents being a conjugate of a carrier with a ligand of the formula:

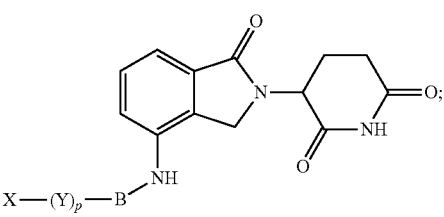

wherein B is —C(=O)—CH2-, —C(=O)—NH—CH2-, —C(=O)—O—CH2- or —CH2-
Y is an organic spacing group;
p is an integer from 0 to 1; and
X is a terminal functional group capable of binding to a carrier;
and the other reagent being an antibody selectively reactive with a mixtures of the pharmaceutically active chemotherapeutic drugs, lenalidomide and thalidomide and having a selective reactivity with thalidomide of at least 10% based upon its reactivity with said mixture of pharmaceutically active chemotherapeutic drugs.

14. The kit of claim 13 wherein p is 1.

15. The kit of claim 14 where Y is lower alkylene.

16. The kit of claim 15 where X is

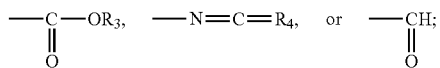

wherein $R_3$ is hydrogen or taken together with its attached oxygen atom forms a reactive ester and $R_4$ is oxygen or sulfur.

17. The kit of claim 16, wherein X is

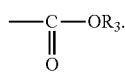

18. The kit of claim 17 wherein Y is